United States Patent
Oh et al.

[11] Patent Number: 6,040,462
[45] Date of Patent: Mar. 21, 2000

[54] CALIX[4]ARENE DIBENZO CROWN ETHERS, THEIR PREPARATION PROCESS AND THEIR USE FOR THE SELECTIVE EXTRACTION OF CESIUM ION

[75] Inventors: Won Zin Oh; Kune Woo Lee; Wang Kyu Choi; Hyun Soo Park, all of Taejon-si; Jong Seung Kim, Choongcheongnam-do; Moon Hwan Cho, Kangwon-do; Jong Kook Kim, Chooncheongnam-do, all of Rep. of Korea

[73] Assignees: Korea Atomic Energy Research Institute, Taejon-si; Korea Electric Power Corporation, Seoul, both of Rep. of Korea

[21] Appl. No.: 09/197,920

[22] Filed: Nov. 23, 1998

[30] Foreign Application Priority Data

Sep. 28, 1998 [KR] Rep. of Korea .................. 98-40327

[51] Int. Cl.[7] ...................... C07D 323/00; C07C 43/205
[52] U.S. Cl. ...................... 549/352; 562/471; 562/500; 568/644
[58] Field of Search .................. 549/352; 562/471, 562/500; 568/644

[56] References Cited

U.S. PATENT DOCUMENTS 4,452,702  6/1984  Blasius et al. .
5,607,591  3/1997  Dozol et al. .

OTHER PUBLICATIONS

Kim, et al., Bull. Korean Chem. Soc. (1997), 18(6) pp. 677–680.

*Primary Examiner*—Johann Richter
*Assistant Examiner*—Taofiq A. Solola
*Attorney, Agent, or Firm*—Bachman & LaPointe, P.C.

[57] ABSTRACT

Novel calix[4]arene dibenzo crown ethers useful to selectively extract cesium are represented by the formula:

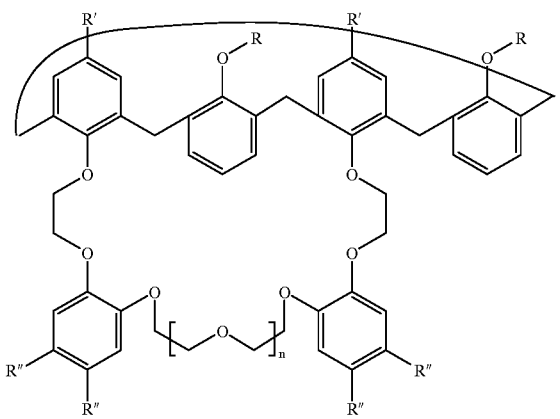

wherein R is a $C_1-C_{10}$ normal alkyl, a phenyl or a methoxyphenyl, R' is hydrogen, p-tert-butyl or a $C_1-C_{10}$ normal alkyl, R" is a $C_1-C_{10}$ normal alkyl, and n is an integer of 0–2. The novel compound is prepared at high yields by introduction of benzene rings into the crown ether ring of calix[4]arene crown-6-ether. The calix[4]arene dibenzo crown ethers are superior in selective absorptivity for cesium ions by virtue of their 1,3-alternate conformational structure and thus, can be used as selective extractants able to separate cesium ions at a high efficiency.

4 Claims, No Drawings

CALIX[4]ARENE DIBENZO CROWN ETHERS, THEIR PREPARATION PROCESS AND THEIR USE FOR THE SELECTIVE EXTRACTION OF CESIUM ION

BACKGROUND OF THE INVENTION

1. Field of the Invention

The present invention relates to calix[4]arene dibenzo crown ether compounds, their preparation process and their use as extractants which can selectively separate cesium ions ($Cs^+$). More particularly, the present invention relates to calix[4]arene dibenzo crown ethers able to selectively extract the cesium ions present in the state of traces in aqueous effluents from nuclear fuel cycle facilities, their preparation process and their use in extraction of cesium ions. Useful as ionophores for separating cesium ions from radioactive wastes, the compounds of the present invention are represented by the following structural formula 1:

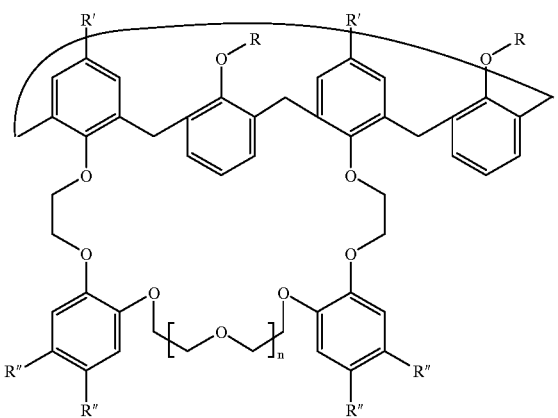

wherein R is a $C_1$–$C_{10}$ normal alkyl, a phenyl or a methoxyphenyl, R' is hydrogen, p-tert-butyl or a $C_1$–$C_{10}$ normal alkyl, R" is hydrogen or a $C_1$–$C_{10}$ normal alkyl, and n is an integer of 0–2.

2. Description of the Prior Art

As industry has been highly advanced, environmental pollution is aggravated. In the present days, nuclear power is extensively used as an important energy source by virtue of its economical favorability in terms of, for example, investment cost in equipment, so more radioactive wastes are now generated mostly from atomic power plants. Therefore, the techniques for disposing radioactive wastes safely and in as little space as possible must be settled without delay.

The concentration technique by evaporation which has been employed for the disposal of radioactive waste liquids thus far, is very good in desalting, but produces a large amount of the wastes to be solidified because it treats all nuclides and salts together. In order to dispose of such wastes, of particularly interest are extractants which are capable of selectively separating heat-generating nuclides and long half-life nuclides. Active and extensive research has been and continues to be directed to the development of the extractants.

A special control is required for cesium upon solidification after disposal of radioactive wastes because it is much longer in half-life (about 30 years) than other fission products, such as cobalt (5.72 years) and iodine (8 days), and generates heat. Thus, if the cesium ions contained in radioactive wastes are selectively separated, a great effect can be brought about on the disposal of radioactive wastes in terms of stability and energy efficiency.

The host-guest chemistry is a science field in which the interaction of the compounds, ions and/or molecules having intramolecular holes is researched. Since 1971 in which *Helv. Chim. Acta*, 54, 268, 1971, issued to professor Moff, describes that most of the ionophores present in nature are able to selectively transport cations through cell membranes, functioning as antibiotics, the chemistry has been of great interest and continues to be utilized in extensive research.

Calixarenes, which have interesting structures, compose a branch of the host-guest chemistry. For the past twenty years, the research in the calixarene chemistry has been focused on the synthesis and structural specificity of calixarenes and their derivatives. Particularly, recent research has reported that the calixarene crown ether compounds based on calix[4]arenes are able to selectively extract the metals such as cesium and be applied for the solidification of the concentrated radioactive waste liquids, which could cause serious problems in the aspect of environmental pollution if they are not treated properly.

The word calixarene is the compound word of calix and arene, both derived from Greek, meaning a benzene ring-containing macrocyclic compound with a shape of a wine cup (Vögtel and Weber, *Host Guest Complex Chemistry Macrocycles*, 378, Springer-Verlag, 1985).

p-tert-Butyl calixarene, representative of calixarenes, was synthesized from the reaction of p-tert-butyl phenol and formaldehyde in the presence of sodium hydroxide, as shown in the following scheme 1 (Cornforth et al., *J. Pharmacol.*, 73, 10, 1995):

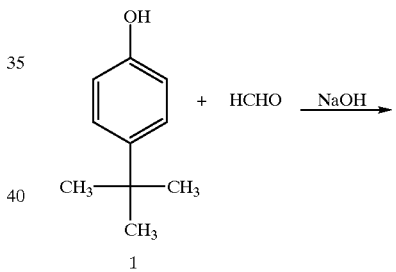

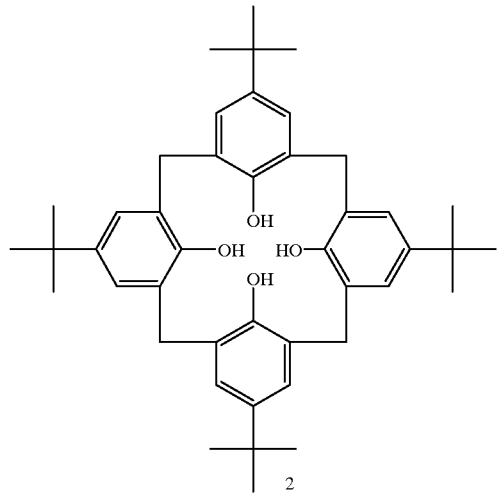

From the p-tert-butylcalix[4]arene 2, Gutsche et al., easily synthesized a calix[4]arene 3 by eliminating the p-tert-butyl group with the aid of an $AlCl_3$ catalyst, as shown in the following scheme 2 (*J. Org. Chem.*, 5795–5802, 50, 1985)

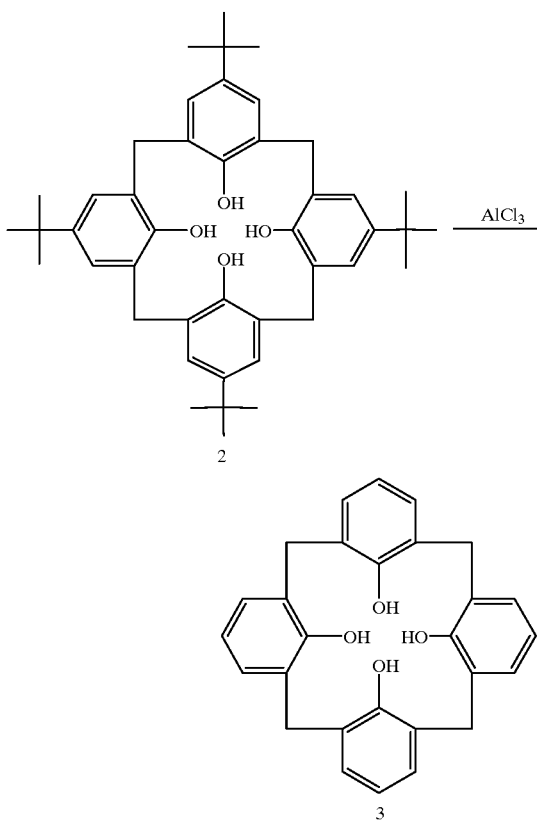

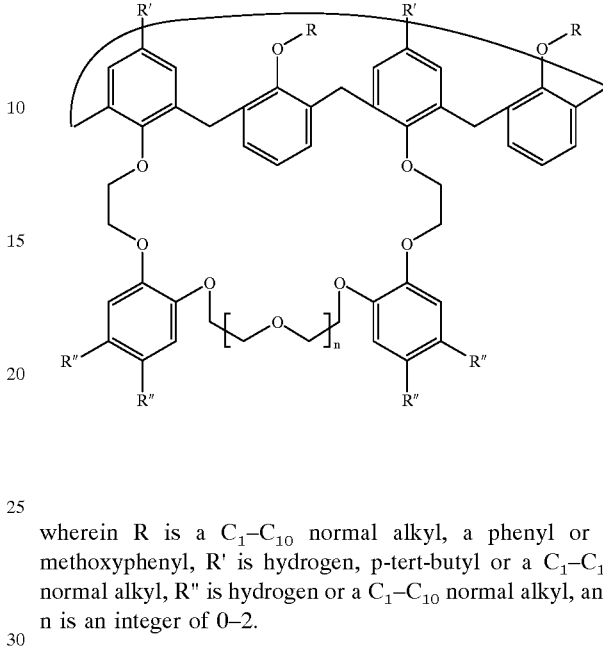

D. N. Reinhoudt et al., succeeded in the synthesis of calix[4]arene-crown-6-ether and the isolation of its four stereoisomers. During a study on the use of these calix arene compounds as macrocyclic ligands to absorb alkali metals, they found that 1,3-alternate calix[4]arene-crown-6-ether is of high selectivity for cesium ions (*J. Am. Chem. Soc.,* 117, 2767, 1995).

Dozol disclosed the synthesis of a biscrown calix[4]arene in PCT/FR93/01161 and a calix[4]arene crown ether in PCT/FR94/00432 and asserted that these macrocyclic ligands were superior in selectivity and efficiency for cesium ions to any other crown ether known. However, these crown ethers are problematic in practical use as an ion extractant because their binding capacity to ions or their ion-extracting performance is reduced.

SUMMARY OF THE INVENTION

The thorough and intensive research on the development of a macrocyclic ligand as a cesium ion extractant, repeated by the present inventors, resulted in the finding that the introduction of benzene rings into the crown ether ring of calix[4]arene crown-6-ether can be accomplished at high yields and improve the selectivity for cesium ions.

Therefore, it is an object of the present invention to overcome the above problems encountered in prior arts and to provide a calix[4]arene dibenzo crown ether, which functions as an organic ligand to segregate cesium ions with high selectivity.

It is another object of the present invention to provide a process for preparing the crown ether at high yield and with ease.

It is a further object of the present invention to provide use of the crown ether in the selective extraction of cesium ions.

In accordance with an aspect of the present invention, there is provided a calix[4]arene dibenzo crown ether capable of selectively extracting cesium ions, represented by the following structural formula 1:

wherein R is a $C_1$–$C_{10}$ normal alkyl, a phenyl or a methoxyphenyl, R' is hydrogen, p-tert-butyl or a $C_1$–$C_{10}$ normal alkyl, R" is hydrogen or a $C_1$–$C_{10}$ normal alkyl, and n is an integer of 0–2.

As a representative example of the compounds of the invention, there is 1,3-dipropyloxy calix[4]arene dibenzocrown-6-ether, which has the structure of the structural formula 1 wherein R is propyl, R' is hydrogen, R" is hydrogen, and n is 0.

The superior selectivity for cesium ions of the calix[4]arene dibenzocrown compounds of 1,3-alternate structure is attributed to two important factors: the crown ether of the present invention provides a cavity within the molecule, which is a right fit for a cesium ion; and, when the crown ether absorbs a cesium ion, the oxygens, functioning as electron-donors, in the crown ether ring and the π electrons of the two benzene rings at 1,3-alternate positions do both facilitate the cation's binding.

The alkyl substituents at the hydroxy positions in the calix[4]arene compounds are preferably of low hydrophobicity. For example, when the dibenzo crown ether compounds of the structural formula 1 meet cesium ions at the interphase between a receiving phase and an organic layer, the alkyl groups of high hydrophobicity give rise to an increase in the solubility of the crown ether compounds in the organic layer, thereby decreasing the release of cesium ions into the receiving phase.

In accordance with another aspect of the present invention, the calix[4]arene dibenzo crown ether compounds of the structural formula 1, can be prepared as adducts from calix[4]arene derivatives and dibenzodimesylates in the presence of cesium carbonate ($Cs_2CO_3$), as shown in the following scheme 3:

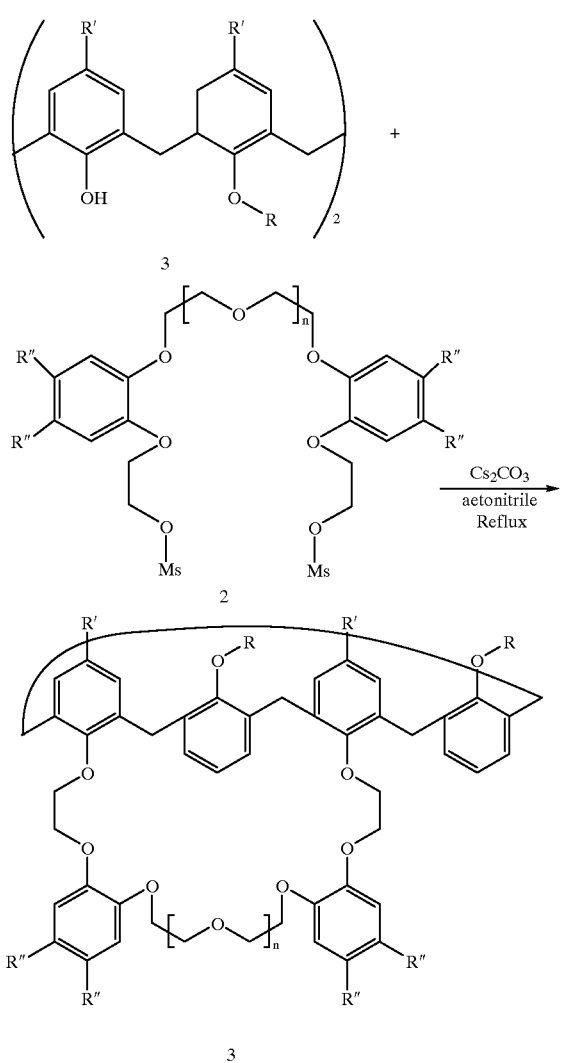

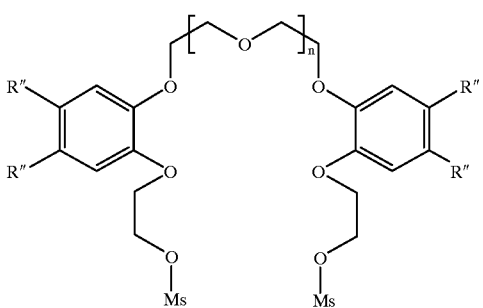

wherein R, R', R" and n are each as defined in the structural formula 1.

In accordance with a further aspect of the present invention, there is provided a selective extractant for cesium ions, comprising the calix[4]arene dibenzo crown ether as an essential ingredient.

DETAILED DESCRIPTION OF THE INVENTION

An equivalent of the calix[4]arene of the structural formula 3 is reacted with 0.5–10 equivalents of the dimesylate of the structural formula 2 in the presence of 1–100 equivalents of cesium carbonate in $1-1\times10^6$ equivalents of a suitable solvent, to give the compounds of the structural formula 1. The reaction is preferably carried out at 0–200° C. for 5 min to 30 days in an inert gas atmosphere, i.e. nitrogen or argon gas atmosphere. Available for the solvent is acetonitrile, methylene chloride, tetrahydrofuran, chloroform, benzene, dioxane or diethylether.

Also, the present invention pertains to a dibenzodimesylate compound, represented by the following structural formula 2, which is used as a precursor for the calix[4]arene dibenzo crown ether;

wherein R" and n are each as defined in the structural formula 1.

The compound of the structural formula 2 can be prepared in the reaction procedure shown in the following

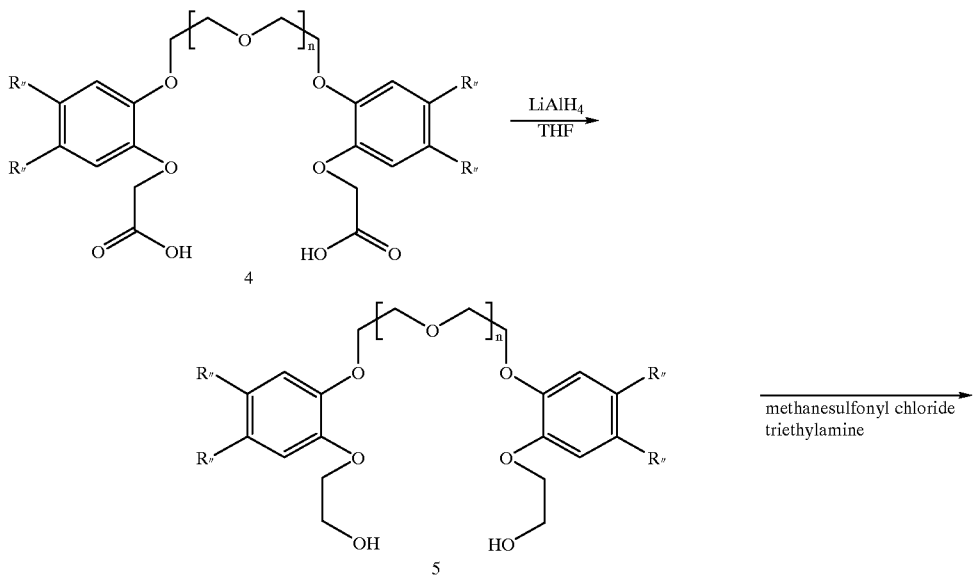

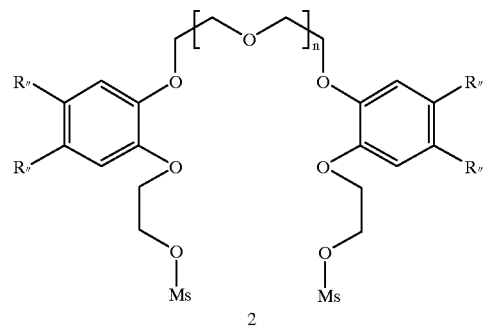

wherein R" and n are each as defined in the structural formula 1. As seen, the preparation of the precursor is accomplished in two steps: an acyclic polyether dicarboxylic acid of the structural formula 4 is reduced into a dibenzo polyether alcohol of the structural formula 5 in the presence of $LiAlH_4$ in a suitable solvent (step 1); and the dibenzo polyether alcohol thus obtained is reacted with methanesulfonyl chloride in the presence of triethylamine to afford a dibenzodimesylate of the structural formula 2 (step 2). In this substitution reaction, an equivalent of the dibenzo polyether alcohol of the structural formula 5 is reacted with 0.5–20 equivalents of methanesulfonyl chloride in the presence of 1–100 equivalents of triethyl amine at −30~200° C. for 5 min–30 days under an inert gas atmosphere, such as nitrogen gas or argon gas. Available solvents for this reaction include methylene chloride, tetrahydrofuran, chloroform, benzene, acetonitrile, dioxane and diethylether.

With superior absorptivity for cesium, the 1,3-alternate calix[4]arene dibenzo crown ether of the present invention is prepared by introducing benzene rings into an ether ring, according to the present invention. The introduction of benzene rings fortifies the ether ring and increases the hydrophobicity of the compounds, thereby greatly improving the solubility in organic phase upon complexation with metal ions. When the dimesylate is added to the calix[4]arene, propyl is preferably recommended as the R group because its steric bulk allows the adduct to easily have a 1,3-alternate conformational structure.

In accordance to another aspect, the present invention pertains to an extractant comprising the calix[4]arene dibenzo crown ether of the structural formula 1 as a macrocyclic ligand capable of selectively separating cesium ions.

A better understanding of the present invention may be obtained in light of the following examples which are set forth to illustrate, but are not to be construed to limit the present invention

EXAMPLE I

SYNTHESIS OF 1,3-DIPROPYLOXY CALIX[4] ARENE DIBENZO CROWN-6-ETHER (Step 1) Synthesis of 1,2-Bis[2-(2-hydroxyethyleneoxy) phenoxy]ethane In 200 ml of tetrahydrofuran was added 3.0 g (75.0 mmol) of $LiAlH_4$ under nitrogen. After being well stirred at 0–20° C., the mixture was added dropwise with a solution of 6.0 g (16.6 mmol) of 1,2-bis[2-(carboxy methoxy)phenoxy] ethane (corresponding to the compound of the structural formula 3 in the scheme 3) in 50 ml of tetrahydrofuran for 30 min in an ice bath. Thereafter, the mixture was further stirred for 30 min and refluxed for 10 hours with stirring.

After the completion of the reaction was confirmed by thin layer chromatography (TLC), addition with 5 ml of ethyl acetate and 5 ml of 10% sodium hydroxide solution in an ice bath gave white precipitates. At room temperature, this mixture was further stirred for 30 min, followed by suction filtration and washing with tetrahydrofuran. The filtrate was concentrated by distillation under reduced pressure and well mixed with 100 ml of methylene chloride and 100 ml of 10% aqueous HCl solution to separate an organic phase. This organic phase was washed with water and dried over anhydrous sodium sulfate. The anhydrous sodium sulfate was filtered off and the organic solvent was removed by distillation under reduced pressure. The residue of the oil phase was purified by recrystallization from diethylether to afford the title compound.

Element analysis for $C_{18}H_{22}O_6$:
Found: C, 64.75; H, 6.60
Calculated: C, 64.73; H, 6.63

Referring to the nuclear magnetic resonance spectra of proton with use of tetramethyl silane (TMS) as a standard, aromatic hydrogens were deduced from the singlet peak at 6.91 ppm, the presence of alcohol hydrogens in an ether chain from the broad peak at 4.72 ppm, 8 hydrogens in the ether chain from the singlet peak at 4.05 ppm, and 4 hydrogens of the ethylene in $ArOCH_2CH_2OAr$ from the singlet peak at 3.23 ppm. In IR spectra with KBr for the compound, an O—H peak and a stretching band for C—O single bond were read at 3,400 $cm^{-1}$ and 1115 $cm^{-1}$, respectively.

(Step 2) Synthesis of 1,2-Bis[2-(2-methanesulfonyloxy ethyleneoxy)phenoxy]ethane In 100 ml of anhydrous methylene chloride was added 4.0 g (13.0 mmol) of the title compound of Step 1 and 3.0 g (29.0 mmol) of triethylamine under nitrogen. After being cooled to 0° C. in an ice bath, the mixture was added dropwise with 3.00 g (26.0 mmol) of methanesulfonyl chloride for 30 min. Thereafter, the resulting mixture was further stirred for 10 hours at elevated temperatures, followed by addition of 50 ml of 5%. sodium hydrogen carbonate to separate an organic layer. This layer was washed twice with 50 ml of saturated brine and dried over anhydrous sodium sulfate. The anhydrous sodium sulfate was filtered off and the organic solvent was removed by distillation under reduced pressure. The residue of the oil phase was purified by recrystallization from diethylether to afford the title compound.

Element analysis for $C_{20}H_{26}O_{10}S_2$:
Found: C, 48.95; H, 5.29
Calculated: C, 48.97; H, 5.31

In the nuclear magnetic resonance spectra of proton with use of TMS as a standard, a multiplet peak was read over 7.01–6.90 ppm, representing eight hydrogens attached to aromatic benzene group. From the triplet peak at 4.55 ppm, it was deduced that four hydrogens were located near the carbon atom of mesylate. The singlet peak read at 4.32 ppm stood for the 4 hydrogens of the ethylene glycol which was located near aromatic benzene. While the triplet at 4.25 ppm represented 4 hydrogens of the first carbons connected to the mesyl groups, the singlet peak at 3.07 ppm represented the 6 hydrogens in the two methyl groups of the mesyl groups. The structure of the compound synthesized was confirmed by the IR spectra with KBr, in which two intensive bands were read at 1590, 1513, 1343 ($SO_2$), and 1173 ($SO_2$) $cm^{-1}$, informing of $SO_2$ stretching.

(Step 3) Synthesis of 1,3-Dipropyloxy calix[4]arene dibenzocrown-6-ether

In 50 ml of acetonitrile were added 1.0 g (2.0 mmol) of 1,3-dipropyloxy calix[4]arene, 1.0 g (2.0 mmol) of 1,2-bis [2-(2-methanesulfonyloxyethyleneoxy)phenoxy]ethane (the title compound of Step 2) and 3.2 g (9.8 mmol) of cesium carbonate under nitrogen and the solution was stirred for 24 hours under reflux. After the reaction was cooled to room temperature, the precipitated cesium carbonate was filtered off and the solvent was removed by distillation under reduced pressure. The residue was dissolved with 50 ml of 10% hydrochloric acid solution and 50 ml of methylene chloride to separate an organic phase. Thereafter, this phase was washed twice with each of 50 ml of 10% hydrochloric acid solution and 50 ml of water and dried over anhydrous sodium sulfate. Following filtering off the anhydrous sodium sulfate, the organic solvent was removed by distillation under reduced pressure to afford the title compound which was, then, obtained as a white crystalline phase from recrystallization from diethylether: Yield ≧90; mp 229–232° C.

Of calix[4]arene crown ethers, the calix arenes having 1,3-alternate conformational structures show a characteristic NMR peak which is read as a singlet peak with an intensity of 8 hydrogens at near 3.80 ppm. Consistent with this, the peak at 3.80 ppm in the NMR spectrum confirmed that the compound has a 1,3-alternate conformational structure.

With reference to the NMR spectra of proton for the compound, the multiplet peaks which were read over 7.12–6.55 ppm represented 16 and 4 hydrogens of the benzene ring. From the singlet peak with an intensity of 4 hydrogens which was read at 4.37 ppm, the ether ring was also confirmed. The multiplet peak with an intensity of 12 hydrogens over 3.65–3.32 ppm resulted from the overlap of the peak from the italicized hydrogens of —O*CH₂CH₂*CH₃ with the peak from the hydrogen of the ether ring. And the singlet peak with an intensity of 8 hydrogens at 3.75 ppm represented hydrogens of methylene connected to benzene rings. The multiplet peak over 1.25–1.16 ppm, with an intensity of 4 hydrogens, was contributed from the italicized hydrogens of —OCH₂*CH₂*CH₃. Finally, the triplet peak at 0.65 ppm with an intensity of 6 hydrogens corresponded to the italicized hydrogens of —OCH₂CH₂*CH₃*. $^{13}C$ NMR: 157.5, 156.7, 152.0, 149.7, 134.8, 134.7, 130.3, 129.9, 124.7, 123.3, 123.0, 122.8, 122.3, 115.9, 72.7, 71.0, 69.0, 68.0, 38.7, 23.3, 10.7 ppm The structure of the compound synthesized was confirmed from the IR spectra with KBr in which peaks were read at 3068 (Ar—H), 1501, 1451, 1254 and 1196 $cm^{-1}$. The compound was found to be 806.11 as measured by mass spectroscopy while its calculated value is 806.21.

Element Analysis for $C_{52}H_{54}O_8$:
Found: C, 77.30; H, 6.71
Calculated: C, 77.41; H, 6.69

EXAMPLE II TO V

The procedure of Example I was repeated using the compounds indicated in Table 1, below.

TABLE 1

| | Substituents | | | |
|---|---|---|---|---|
| Examples | R | R' | R" | n |
| II | Propyl | H | H | 1 |
| III | Butyl | H | H | 1 |
| IV | Octyl | H | H | 1 |
| V | Propyl | H | H | 2 |

EXPERIMENT EXAMPLE

Assay for the Selective Absorptivity of Calix[4] Arene Dibenzo Crown Ether for Cesium Ions Using Bulk Liquid Membrane Method To test the calix[4]arene dibenzo crown ethers of the present invention for selectivity for cesium ions, the bulk liquid membrane method, as described in *Bull. Korean Chem. Soc.*, 16, p33, 1995, issued to Cho, Moon-Hwan et al., was employed.

With being of recent interest, the bulk liquid membrane method is used for separating particularly the metals contained in waste water. According to the method, an organic solvent is introduced between a source phase and a receiving phase and the ligands solubilized in the organic solvent play a role as a metal eliminator by transferring the metal ions from the source phase to the receiving aqueous phase.

In this example, the compounds of the present invention were compared in selective absorptivity for cesium ions with a well-known compound, i.e., 1,3-dipropyloxy calix[4]arene crown-6-ether of the following structure, which was synthesized in a known process.

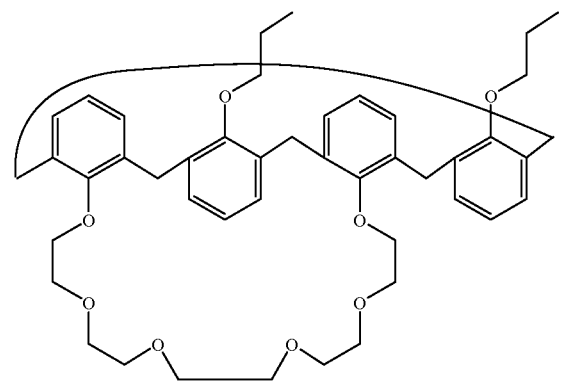

The bulk liquid membrane method was carried out as follows. In a lower part of a cylindrical tube was introduced a 0.001 M solution of the compounds of the invention or the control in 3 ml of chloroform. In the outer upper part of this organic phase, a solution containing 0.8 ml of each of 0.1 M $LiNO_3$, 0.1 M $NaNO_3$, 0.1 M $KNO_3$, 0.1 M $RbNO_3$ and 0.1 M $CsNO_3$ were charged as a source phase while 5 ml of deionized distilled water was charged as a receiving phase in the inner upper part of the organic phase. The system was stirred with a Teflon magnetic bar 13 mm long. This procedure was repeated three times or more. For comparison of ion mobility, an organic phase without the compounds of the structural formula 1, was used as a control. The metal amounts transferred were represented by the mole flux as calculated in the following equation:

$$\text{Mole Flux} = \frac{\text{transferred moles}}{\text{sec} \times m^2}$$

In this equation, the mole flux is defined as the mole number of the metal which is transferred per time per area. The mobility was reduced into the unit $10^{-8}$ mole.s$^{-1}$.m$^{-2}$ for use. The results are given in Table 2, below.

TABLE 2

| Compounds | Mole Flux ($10^{-8}$ mole · s$^{-1}$ · m$^{-2}$) | | | | |
| --- | --- | --- | --- | --- | --- |
|  | Li$^+$ | Na$^+$ | K$^+$ | Rb$^+$ | Cs$^+$ |
| Control | 0.00 | 0.82 | 2.01 | 21.6 | 43.6 |
| Example I | 0.00 | 1.51 | 2.84 | 44.95 | 130.59 |
| Example II | 0.00 | 1.92 | 1.28 | 2.35 | 11.87 |
| Example III | 0.00 | 0.60 | 0.64 | 1.37 | 8.12 |

As described hereinbefore, the calix[4]arene dibenzo crown ether compounds of the present invention are superior in selective absorptivity for cesium ions by virtue of their 1,3-alternate conformational structure. In addition, the compounds can be prepared at a high yield, according to the process of the present invention which comprises the reaction of calix[4]arene derivatives with dimesylates in the presence of cesium carbonate. Consequently, the calix[4] arene dibenzo crown ethers prepared according to the present invention can be used as selective extractants able to separate cesium ions at a high efficiency.

What is claimed is:

1. A calix[4]arene dibenzo crown ether capable of selectively extracting cesium ions, represented by the following structural formula 1:

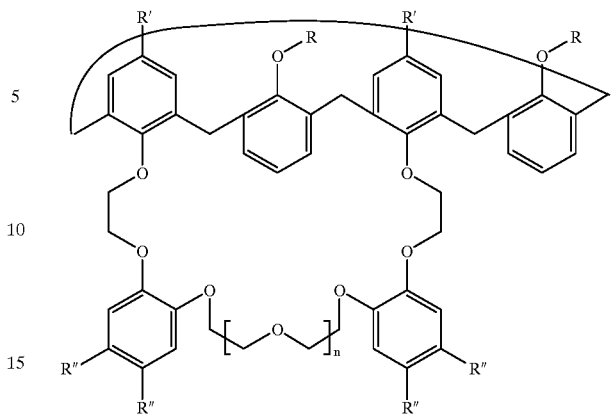

wherein R is a $C_1$–$C_{10}$ normal alkyl, a phenyl or a methoxyphenyl, R' is hydrogen, p-tert-butyl or a $C_1$–$C_{10}$ normal alkyl, R" is hydrogen or a $C_1$–$C_{10}$ normal alkyl, and n is 0.

2. A calix[4]arene dibenzo crown ether as set forth in claim 1, wherein R is propyl, R' is hydrogen, R" is hydrogen and n is zero.

3. A dibenzodimesylate useful as a starting material to prepare the calix[4]arene dibenzo crown ether of claim 1, represented by the following structural formula 2:

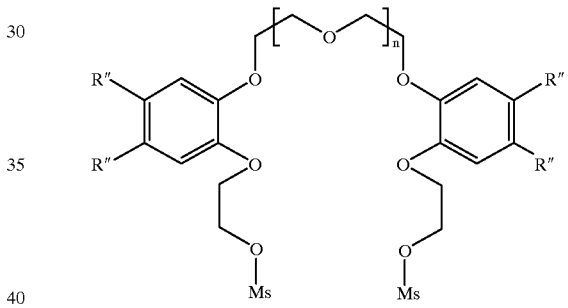

wherein R" is hydrogen or a $C_1$–$C_{10}$ normal alkyl where Ms is a methanesulfonyl, and n is 0.

4. A selective extractant for cesium ions, comprising the calix[4]arene dibenzo crown ether of claim 1 as an essential ingredient.

* * * * *